United States Patent
Korb et al.

(10) Patent No.: US 9,775,344 B2
(45) Date of Patent: Oct. 3, 2017

(54) HIGH ALCOHOL CONTENT SANITIZER

(71) Applicant: Donald R. Korb, Boston, MA (US)

(72) Inventors: Donald R. Korb, Boston, MA (US); Hridaya N. Bhargava, Sharon, MA (US)

(73) Assignee: Donald R. Korb, Boston, MA (US)

( * ) Notice: Subject to any disclaimer, the term of this patent is extended or adjusted under 35 U.S.C. 154(b) by 0 days.

(21) Appl. No.: 14/886,902

(22) Filed: Oct. 19, 2015

(65) Prior Publication Data

US 2016/0081333 A1    Mar. 24, 2016

Related U.S. Application Data

(62) Division of application No. 13/403,259, filed on Feb. 23, 2012, now Pat. No. 9,161,531.

(60) Provisional application No. 61/446,008, filed on Feb. 23, 2011.

(51) Int. Cl.
| | |
|---|---|
| *A61K 9/00* | (2006.01) |
| *A01N 31/02* | (2006.01) |
| *A61K 8/34* | (2006.01) |
| *A61K 8/55* | (2006.01) |
| *A61Q 17/00* | (2006.01) |
| *A01N 25/04* | (2006.01) |
| *A61K 8/37* | (2006.01) |
| *A61K 8/97* | (2017.01) |
| *A61Q 19/00* | (2006.01) |

(52) U.S. Cl.
CPC .............. *A01N 31/02* (2013.01); *A01N 25/04* (2013.01); *A61K 8/34* (2013.01); *A61K 8/37* (2013.01); *A61K 8/553* (2013.01); *A61K 8/97* (2013.01); *A61Q 17/005* (2013.01); *A61Q 19/007* (2013.01); *A61K 2800/48* (2013.01); *A61K 2800/49* (2013.01); *A61K 2800/596* (2013.01); *A61K 2800/74* (2013.01)

(58) Field of Classification Search
CPC ...... A01N 31/02; A01N 25/04; A61Q 17/005; A61Q 19/007; A61K 8/34; A61K 8/37; A61K 8/553; A61K 8/97; A61K 2800/48; A61K 2800/49; A61K 2800/74; A61K 2800/596
See application file for complete search history.

(56) References Cited

U.S. PATENT DOCUMENTS

| | | |
|---|---|---|
| 3,755,560 A | 8/1973 | Dickert et al. |
| 4,421,769 A | 12/1983 | Dixon et al. |
| 4,464,400 A | 8/1984 | Kimura et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 4,914,088 A | 4/1990 | Glonek et al. |
| 5,011,681 A | 4/1991 | Ciotti et al. |
| 5,100,660 A | 3/1992 | Hawe et al. |
| 5,278,151 A | 1/1994 | Korb et al. |
| 5,294,607 A | 3/1994 | Glonek et al. |
| 5,302,377 A | 4/1994 | Pereira et al. |
| 5,371,108 A | 12/1994 | Korb et al. |
| 5,578,586 A | 11/1996 | Glonek et al. |
| 5,581,543 A | 12/1996 | Natarajan |
| 5,652,274 A | 7/1997 | Martin |
| 5,738,856 A | 4/1998 | Korb et al. |
| 6,440,456 B1 | 8/2002 | Nguyen et al. |
| 6,524,614 B2 | 2/2003 | Cannell et al. |
| 7,683,018 B2 | 3/2010 | Koivisto et al. |
| 2005/0129626 A1 | 6/2005 | Koivisto et al. |
| 2006/0281663 A1 | 12/2006 | Asmus |
| 2008/0138296 A1 | 6/2008 | Tamarkin et al. |
| 2009/0082472 A1 | 3/2009 | Peters |
| 2009/0226498 A1 | 9/2009 | Flugge-Berendes et al. |

FOREIGN PATENT DOCUMENTS

CN    101381656 A    3/2009

OTHER PUBLICATIONS

Purell, "Instant Hand Sanitizer with a Touch of a Lubriderm Moisturizer," www.purell.com, 2010, 1 page.
"Sanitizing, Hand Sanitizer Moisurizer, The Sanitizer that Loves Your Hands," www.goldbondultimate.com/hand-sanitizer-moisturizer.html, 2011, 1 page.
Tzen, JTC et al., Lipids, Protein, and Structure of Seed Oil Bodies from Diverse Species, Plant Pyshiology, 1993, 101: pp. 267-276.

*Primary Examiner* — David Browe
(74) *Attorney, Agent, or Firm* — Slater Matsil, LLP

(57) ABSTRACT

An antimicrobial sanitizing composition in the form of a gel or cream containing an alcohol in an amount of at least 55% by weight. The sanitizer is capable of disinfecting a variety of surfaces, including the skin. In addition to alcohol, the sanitizer contains an anionic phospholipid in a controlled concentration as well as components conventionally found in skin creams and gels such as emulsifiers, emollients, moisturizers, rheology modifiers, and neutralizers.

26 Claims, No Drawings

HIGH ALCOHOL CONTENT SANITIZER

This application is a divisional of U.S. patent application Ser. No. 13/403,259, filed on Feb. 23, 2012, entitled "High Alcohol Content Sanitizer," which claims the benefit of U.S. Provisional Application No. 61/446,008, filed on Feb. 23, 2011, entitled "High Alcohol Content Sanitizer," which applications are hereby incorporated herein by reference.

TECHNICAL FIELD

The present invention relates generally to a cream or gel like antimicrobial sanitizer for use on a variety of surfaces including the skin. The sanitizer contains an antibacterial concentration of alcohol. The sanitizer is capable of use on the skin without irritation and without leaving an undesirable oily or greasy layer on the skin's surface.

BACKGROUND

It is known that antimicrobial hand sanitizers containing a high concentration of alcohol are effective in killing microorganisms when used by routinely washing one's hands with the sanitizer. Although alcohol-containing sanitizers are known to possess good antimicrobial activity and prevent infections, such sanitizers typically require the use of a minimum of from 60% of an alcohol such as ethanol to be effective. However, use of alcohol on the skin at these concentrations often severely dries the skin as the alcohol dissolves the sebum from the skin. Consequently, continuous use of such products can leave the user's skin dry, often resulting in red, chapped, and cracked skin.

To prevent a user's skin from drying due to use of a high alcohol content sanitizer, many such products include moisturizers, for example, humectants and emollients, as additional components in their formulations. While providing some protection against drying of the skin, there are disadvantages to the use of these sanitizers due to the addition of the moisturizers. For example, conventional sanitizers containing moisturizers or other hydrophobic skin protectants are unstable and tend to break down over time. As a result, the added moisturizers or skin protectants do not remain distributed throughout the sanitizer whereby the moisturizing ability of the sanitizer becomes ineffective. Additionally, the instability of the sanitizers may cause the formation of large oil layers on the skin and, as a result, the sanitizer may feel greasy and not aesthetically pleasing when applied to the skin.

The adverse effects on the skin resulting from the use of sanitizers containing a high concentration of alcohol are more fully described in U.S. Pat. No. 7,683,018 and in U.S. Patent Publication Number 2009/0226498. These publications also describe the difficulties encountered when moisturizers or other hydrophobic skin protectants are added to such compositions.

The invention of U.S. Pat. No. 7,683,018 is described as an antimicrobial high alcohol content composition in the form of a gel or foam. It is stated that compositions that foam when dispensed from a suitable dispenser are stable and do not require the use of propellants and pressurized containers. The gels are described as having a viscosity of less than 4,000 cps as they specifically exclude gelling or thickening agents of the type typically found in commercial gels and creams. According to the disclosure of said patent, after single or multiple applications of the gel, there is no tacky or sticky after-feel and the gel does not clog the dispensers from which the gels are dispensed. To the extent that this is so, it is believed that the absence of gelling or thickening agents and the control of composition viscosity may contribute to the absence of a tacky feel. However, it is also believed that the absence of gelling or thickening agents from the formulations result in reduced consumer appeal.

The invention of U.S. Patent Publication Number 2009/0226498 relates to antimicrobial hand sanitizers that include alcohols and a high internal phase emulsion. The internal phase emulsion is stated to permit moisturizers or skin protectants, such as emollients and/or silicones, to be stably incorporated into the sanitizer. The internal phase emulsion has an aqueous phase in an amount of about 30% (by weight of the emulsion) or less. It is stated that due to the use of the internal emulsion phase, the sanitizer has antimicrobial efficacy and a good moisturizing effect. It is further stated that by incorporating the moisturizer or skin protectant into the alcohol-based hand sanitizer as part of a high internal phase emulsion, the moisturizer or skin protectant remains substantially uniformly distributed throughout the sanitizer for extended periods of time and does not separate out as a separate phase. It is speculated in the application that the reason for this stability is that the emulsion has a mean droplet size of about 5 microns or less allowing droplets to remain suspended throughout the sanitizer for the extended period of time. To formulate the sanitizer, it is necessary to prepare the emulsion separately from the remaining components of the sanitizer. Methods used to prepare the emulsions include the use of high pressure/high shear mixing conditions. Following preparation of the emulsion, it is combined with the other sanitizer components at room temperature by mixing. Disadvantages that might be associated with the sanitizer of the referenced application include the high cost of manufacture and the possibility of instability due to breaking of the emulsion over prolonged time, especially during storage and shipment in adverse weather conditions.

The invention described herein is a high alcohol content antimicrobial gel or cream that contains moisturizing components as well as thickening or gelling agents. When used, the sanitizer destroys bacteria; moisturizes the skin thereby avoiding red, chapped, and cracked skin; and does not leave an oily residue and a tacky feel on the skin. It is believed that these advantages result from the addition of certain phospholipids to the composition in controlled concentration.

The use of phospholipids in skin cream formulations is known and plays a significant role in the cosmetics and pharmaceutical industries because of their stated outstanding physiological properties, such as, for example, emulsifying, softening, and anti-oxidant effects.

U.S. Pat. Nos. 6,440,456 and 6,524,614 disclose the use of phospholipids in delivery compositions for the purposes of solubilizing insoluble components into the composition. Amongst the cosmetic products described in this patent improved by the addition of phospholipids are shampoos, conditioners, deep treatments for hair, body washes, bath gels, hair dyeing compositions, permanent wave formulations, relaxers, make-up preparations, particularly mascara and foundation, and skin creams or lotions. The majority of the working examples within the patent are directed to hair treatment compositions.

In Chinese Patent No. 101381656 (A) (Method for Preparing Soya Bean Lecithin Hand Cleanser) having a publication date of Mar. 11, 2009, a soybean phospholipid hand sanitizer is disclosed. The sanitizer is said to be a foam, but does not contain an alcohol. The soybean phospholipid used is a mixture of phospholipids comprising cationic and non-ionic phospholipids in addition to anionic phospholipids.

The total concentration of the phospholipid in the sanitizer is from 0.4 to 0.5% by weight of the formulation.

U.S. Pat. No. 4,464,400 is directed to a skin care base material for external use where the invention is said to be the use of a phospholipid in combination with an ester of a fatty acid and a polyoxyethylene fatty acid ester. In accordance with the patent, it was found that a skin care base material for external use having adequate stability and providing a "good feel" when applied to the skin is obtained by combining a phospholipid with the ester of a fatty acid and the ester of a polyoxyethylene fatty acid. It is stated that the preferred amount of the phospholipid may range between 0.10 to 20% by weight, preferably from 0.2 to 6% by weight, based upon the weight of the entire composition. Phospholipids disclosed include non ionics, anionics and cationics. The patent also discloses that various other components may be incorporated into the formulation to obtain an aqueous mixture, such as a solution, a colloidal solution, an emulsified lotion, a hydrophilic cream or an aqueous gel, where the aqueous phase constitutes a continuous phase, or an oil mixture such as a water in oil cream or solution. Disclosed components include those commonly used for cosmetics or medicines for external use, such as an oil-and-fat component, an emulsifier, a dispersant, a gelating agent, a chelating agent, a perfume, a vitamin, an anti-inflammatory agent and a moisture maintaining agent such as urea.

Skin cream compositions containing anionic phospholipids are disclosed in U.S. Pat. Nos. 5,738,856 and 5,581,543, each incorporated herein by reference. The invention of said patents is described as a topical treatment composition for skin disorders. It comprises a compound in a pharmaceutically acceptable carrier for topical delivery to the skin that penetrates the epithelial surface to provide prolonged lubrication and moistening. The invention is said to be based upon the discovery that in order to provide prolonged lubrication and moistening of the skin, it is desirable to replicate and replenish the bilayer lamellae naturally occurring in healthy skin. To accomplish this, a formulation is disclosed that is a pharmaceutically acceptable topical carrier containing a compound having one or more polar terminus groups and one or more non-polar terminus groups where the polar and non-polar groups are separated from each other by a spacer segment, referred to in the patents as a bilayer component. Suitable bilayer components disclosed are phospholipids and triglycerides. Negatively charged phospholipids—i.e., anionic phospholipids, are said to be a preferred bilayer component.

Promotional materials for commercial products also identify the use of phospholipids in cosmetic compositions. For example, in a promotional publication entitled "Sanitizing—Hand Sanitizer Moisturizer", [available at website HTTP://www.goldbondultimate.com/hand-sanitizer-moisturizer.html] used in connection with the sale of a commercially available hand sanitizer moisturizer sold under the Trade Name "Gold Bond Ultimate", it is stated that the formulation contains a "Phospholipid Complex that helps restore your skin's lipid layer." Similarly, a product identified as Purell Instant Hand Sanitizer with a Touch of a Lubriderm Moisturizer (uses: for hand washing to decrease bacteria on the skin, recommended for repeated use) identifies a phospholipid as one of its components. The label on its container identifies U.S. Pat. Nos. 5,302,377 and 5,652,274 as patents relating to the product.

Notwithstanding the frequent use of phospholipids in cosmetic compositions as disclosed in the above publications, none of the above publications disclose a formulation having a phospholipid in a product having a high alcohol concentration suitable for use as a hand sanitizer.

SUMMARY

As described above, the sanitizing antimicrobial compositions of the subject invention are emulsions in the form of a gel or cream containing an alcohol in an amount of at least 55% by weight, preferably at least 60% by weight, as a primary antimicrobial component. The sanitizer disinfects and provides prolonged antimicrobial properties to a variety of surfaces. When applied to the skin, it does so without drying of the skin or causing irritation to the skin. In addition to the alcohol, the sanitizer contains an anionic phospholipid component in a controlled concentration plus additional components conventionally found in skin creams and gels such as emulsifiers, emollients, moisturizers, rheology modifiers, pH adjustors, and neutralizers. The phospholipid is believed to stabilize the formulation and contribute to elimination of a tacky feel following application of the sanitizer to the skin.

DETAILED DESCRIPTION OF ILLUSTRATIVE EMBODIMENTS

An antimicrobial sanitizer in accordance with a preferred embodiment of the invention will have a formulation in weight percent as follows:

|  | Preferred | Most Preferred |
| --- | --- | --- |
| Alcohol | 55 to 95 | 60 to 75 |
| Phospholipid | 1.0 to 3.0 | 1.5 to solubility limit |
| Emollient | 1.0 to 8.0 | 3.0 to 6.0 |
| Rheology Modifier | 2.5 to 8.0 | 3.5 to 6.5 |
| Emulsifier | 0.1 to 3.5 | 0.5 to 2.5 |
| Water | to 100 | to 100 |

As will be explained in greater detail below, the sanitizer may be formulated using an anionic phospholipid or a phospholipid that contains an anionic phospholipid as one of its components. Therefore, the concentration range given above for the phospholipid define a range which may be all anionic phospholipid, or a phospholipid where a portion of the phospholipid is anionic provided the anionic portion is present in an amount of from 0.10 weight percent to 3.0 percent of the sanitizer, and more preferably, from 0.25 weight percent to 2.5 percent. In addition, the solubility limit of the phospholipid depends upon the total composition of the sanitizer and will vary with composition. As a guideline, the upper limit would be approximately 3.5 weight percent of the formulation.

In addition to the above, the formulation desirably contains a pH adjustor to maintain pH of the formulation above at least 6.8 and more preferably, within a range of from pH 7.0 to 8.0 and more preferably, from pH 7.25 to 7.75. In addition to the above components, other incidental additives may be present in the formulation typically found in skin cream formulations such as vitamins, fragrances, etc.

The alcohol used in the antimicrobial formulation is desirably a lower hydrocarbon chain alcohol having from 1 to 4 carbon atoms. The preferred alcohol is ethanol, though 2-propanol, or n-propanol, and mixtures, are well accepted by Health Care personnel as an adequate disinfectant at the right percentages. A single alcohol is preferred. As aforesaid, the concentration of the alcohol is at least 55 weight percent but most preferably, is in the clinically prescribed concentration range of from 60 to 65%.

The use of an anionic phospholipid in the sanitizer composition of the invention is responsible for the beneficial results described above. Phospholipids are well-known to those skilled in the art and a discussion of phospholipids can be found in Lehninger, Biochemistry, 2 Ed., Worth Publishers, New York, pp. 279-306; Kirk-Othmer, Concise Encyclopedia of Chemical Technology, John Wiley and Sons, New York, pp. 458-459, 1985 incorporated herein by reference. As is known in the art, the phospholipids differ in size, shape and the charge of their polar head groups. They may be anionic, cationic or non ionic. A negatively charged phospholipid at neutral pH is known as an anionic phospholipid.

Of the phospholipids, anionic phospholipids are included in the sanitizer for purposes of this invention. However, the anionic phospholipid is most often used in the sanitizer formulation in combination with other phospholipids. Examples of anionic phospholipids include dimyristoylphosphatidylglycerol, dipalmitoylphosphatidylglycerol, distearoylphosphatidylglycerol, dioleoylphosphatidylglycerol, oleoylpalmitoylphosphatidylglycerol, dipalmitoylphosphatidylserine, dioleoylphosphatidylserine, dimyristoylphosphatidylinositol, dipalmitoylphosphatidylinositol, phosphatidylethanolamine, distearoylphosphatidylinositol, dioleoylphosphatidylinositol, dimyristoylphosphatidylserine, and distearoylphosphatidylserine. Of these materials, phosphoglycerides and phosphatidyethanolamine are the preferred phospholipids.

Phospholipids are poorly soluble in the sanitizer formulation and as their concentration increases, it becomes increasingly difficult to dissolve and distribute it within the sanitizer. If the total phospholipid content exceeds its solubility limit and is incompletely solubilized, it may be present as a separate phase resulting in a tacky feel to the skin following use of the sanitizer. The solubility limit will vary dependent upon the formulation as a whole but typically has an upper limit in the sanitizer of approximately 3.5 weight percent.

It is believed that pure anionic phospholipids are not commercially available in volume in the marketplace but can be purchased as a specialty item. Therefore, the cost to acquire an anionic phospholipid for preparation of commercially significant volumes of sanitizer would be prohibitive. Phospholipid compositions including an anionic phospholipid in concentrations varying between 8 and 30% of a phospholipid mixture are commercially available in adequate volume and at a suitable price and other phospholipids with differing anionic phospholipid contents are also available at differing price. With respect to the concentration range for the total phospholipid in the sanitizer given above, and taking into consideration the limited solubility of the phospholipid in the sanitizer, it should be apparent that the phospholipid concentration limit applies both to the anionic phospholipid, if used as the sole phospholipid component, and to the total phospholipid content of the sanitizer when the anionic phospholipid is only a portion of the phospholipid additive. In other words, if the phospholipid used is 100% anionic phospholipid, then the concentration range given for the phospholipid applies to the anionic phospholipid. However, if the anionic phospholipid comprises only a portion of the phospholipid additive, then the concentration range given above applies to the entire phospholipid additive provided that the anionic phospholipid portion is present in the phospholipid additive in an amount of from 0.10 weight percent to 3.0 percent of the sanitizer, and more preferably, from 0.25 weight percent to 2.5 percent. If the anionic phospholipid used is part of a phospholipid mixture, then it is desirable to use a mixture that does not contain a cationic phospholipid as cationic phospholipids are not compatible with anionic phospholipids. This may result in phase separation and a sticky feel after multiple uses of the sanitizer.

The phospholipid component is the additive that permits formulation of a high alcohol content sanitizer capable of use without causing skin irritation or dryness. For this reason, the higher the anionic phospholipid portion of the phospholipid additive, the more efficacious will be the sanitizer. When a phospholipid is used having a high concentration of the anionic component, the mid to lower end of the concentration range is adequate though better results are achieved with higher concentrations. When a phospholipid is used having a low anionic phospholipid component, the higher end of the concentration level is used though caution must be exercised to not exceed its solubility limit within the sanitizer.

In addition to the alcohol, the sanitizer contains conventional skin care additives such as emollients, emulsifiers, rheology modifiers, pH adjustors and other conventional components such as fragrances, vitamins, etc.

An emollient acts to soften, soothe, and otherwise moisturize the skin. Suitable emollients that can be incorporated into the sanitizer include oils such as petrolatum based oils, petrolatum, vegetable based oils, mineral oils, natural or synthetic oils, lanolin and its derivatives, aloe, fatty esters, glycerol esters and derivatives, propylene glycol esters and derivatives, alkoxylated carboxylic acids, alkoxylated alcohols, fatty alcohols, fatty acids, and combinations thereof. Suitable esters could include cetyl palmitate, stearyl palmitate, cetyl stearate, isopropyl laurate, isopropyl myristate, isopropyl palmitate, and combinations thereof. The fatty alcohols could include, but not be limited to, octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients. Suitable natural fats or oils include fats, oils, essential oils, essential fatty acids, non-essential fatty acids, phospholipids, and combinations thereof. These natural fats and oils can provide a source of essential and non-essential fatty acids to those found in the skin's natural barrier. Specific examples of suitable natural fats or oils can include citrus oil, olive oil, avocado oil, apricot oil, babassu oil, borage oil, camellia oil, canola oil, castor oil, coconut oil, corn oil, cottonseed oil, emu oil, evening primrose oil, hydrogenated cottonseed oil, hydrogenated palm kernel oil, maleated soybean oil, meadowfoam oil, palm kernel oil, peanut oil, rapeseed oil, grapeseed oil, safflower oil, sphingolipids, seed almond oil, tall oil, lauric acid, palmitic acid, stearic acid, linoleic acid, stearyl alcohol, lauryl alcohol, myristyl alcohol, behenyl alcohol, rose hip oil, calendula oil, chamomile oil, eucalyptus oil, juniper oil, sandlewood oil, tea tree oil, sunflower oil, soybean oil, thyme oil, and combinations thereof. The preferred emollients are fatty esters and isopropyl-palmitate and isopropyl-myristate are most preferred.

The rheology modifier, or for purposes of the invention described herein, thickener, is a material used to alter the viscosity of the formulation. Such materials are conventionally used in cosmetic skin care compositions. For purposes of this invention, the rheology modifier is a thickener used to increase the viscosity of the sanitizer without significantly modifying the efficacy of the composition.

Examples of suitable thickening agents include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids and cellulosic polymers. Examples of commercially available carboxylic acid polymers include carbomers, which are homopolymers of acrylic acid crosslinked with allyl ethers of sucrose or pentaerytritol (e.g., Carbopol.™. 900 series from B. F. Goodrich). Examples of crosslinked polyacrylate polymers include cationic and nonionic polymers. Additional examples are described in U.S. Pat. Nos. 5,100,660; 4,849,484; 4,835,206; 4,628,078; 4,599,379, each incorporated herein by reference.

Examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Examples of cellulosics include carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Examples of gums and polysaccharides that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Of the rheology modifiers described above, carbomers, homopolymers of acrylic acid crosslinked with allyl ethers of sucrose or pentaerytritol, are preferred. The rheology modifier is used in accordance with the ranges given above which produce a gel or cream having a viscosity of at least 2500 cps, preferably at least 3000 cps and most preferably, a viscosity within the range of 3200 to 4000 cps.

The composition of the sanitizer also includes an emulsifier. Emulsifiers, or surfactants, reduce the interfacial tension between phases and improve the formulation and stability of an emulsion. The emulsifiers can be nonionic, anionic, and zwitterionic emulsifiers (See McCutcheon's (1986); U.S. Pat. Nos. 5,011,681; 4,421,769; 3,755,560) though non-ionic and anionic emulsifiers are preferred. Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, triethanolamine (TEA) stearate, diethanolamine (DEA) oleth-3 phosphate, polyethylene glycol 20 sorbitan monolaurate (polysorbate 20), sorbitan monstearate Span 60, polyethylene glycol 5 soya sterol, steareth-2, steareth-20, steareth-21, ceteareth-20, polypropylene glycol 2 (PPG-2) methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

In addition to the above, the sanitizer of the invention includes additional additives found in other skin care products employed in dermatological and cosmetic ointments and lotions. For example, pH adjustors and buffers such as sodium hydroxide and sodium citrate are used as necessary to maintain pH of at least 6.8 and preferably within a range 7.0 to 8.0. If the pH has to be adjusted lower, an acid may be used. Other incidental additives include excipients; fragrances such as menthol; opacifiers such as zinc oxide, magnesium aluminum silicate and titanium dioxide; preservatives such as dichlorobenzyl alcohol, benzoic acid, methylparaben and phenyl carbinol; antioxidants; gelling agents such as petrolatum and mineral wax; thickening agents such as carboxymethylcellulose; stabilizers; surfactants; emollients; coloring agents and the like may be present in the carrier. The CTFA International Cosmetic Ingredient Dictionary, 6th Edition, 1995 details a wide variety of nonlimiting cosmetic ingredients commonly found in skincare products that are suitable for use herein.

The process for preparation of the sanitizer of the invention is a routine two-step process and is in accordance with known procedures for formulation of skin creams. The surfactants, anionic phospholipid, emollients, and other incidental additives soluble in alcohol are added to the alcohol. The mixture is slowly heated to a relatively low elevated temperature, preferably about 30° C., and mixed until a homogeneous solution is obtained. This may take from about 1 to 3 hours dependent upon the solubility of the components of the formulation in the alcohol. Once a homogeneous solution is formed, it is allowed to cool to room temperature. A separate solution is then formed using water and water soluble components such as moisturizers. This solution is mixed until all ingredients are solvated and the solution is homogeneous, typically for from 30 minutes to 1 hour. The two solutions are then combined, a rheology modifier is added and the solution is vigorously agitated until homogeneous, typically for about 1 to 3 hours. Finally, the resulting sanitizer is adjusted to the desired pH.

Example 1: Comparison of Sanitizer to Purell Commercial Product

A comparison between two hand sanitizers was made, one commercially marketed as Purell® Instant Hand Sanitizer and the other, the sanitizer disclosed herein, for simultaneous bactericidal activity and moisturizing.

Each of the Purell and the sanitizer of this example were prepared in identical 2 ounce opaque bottles. Purell® Instant Hand Sanitizer was purchased commercially and repacked in the 2 ounce opaque bottle. The labeling for both were identical, with the exception that one bottle was labeled "O" while the other "V". The code "O" was used to identify the sanitizer disclosed herein and "V" was used for the Purell® sample. The test used 11 general public participants that did not know the meaning of the above codes.

The sanitizer identified as O was prepared following the procedures described above and had the following composition:

| Component | Amount [gms] | Function |
| --- | --- | --- |
| Ethanol 95% | 63.0 | antimicrobial agent |
| Polysorbate 60 [1] | 0.75 | emulsifier |
| Span 60 [2] | 0.50 | emulsifier |
| Phospholipon 75 [3] | 1.5 | phospholipid |
| Isopropyl Myristate | 5.0 | emollient |
| Vitamin E acetate | 0.01 | additive |
| Aloe vera 200X | 0.05 | moisturizer |
| Carbopol Aqua SF-1 [4] | 5.0 | rheology modifier |
| Amino methyl propanol | 0.19 | pH adjustor |
| Water DI q.s. to | 100.00 gm | diluent |

[1] Polyoxyethylene sorbitan monostearate.
[2] Sorbitan monooctadecanoate available from Whyte Chemicals.
[3] Mixture of phospholipids containing approximately 72% phosphatidyl choline, 2% lysophosphatidyl choline, 10% phosphatidylethanolamine - the anionic phospholipid, with the balance phosphorus and other lipid oils.
[4] acrylates copolymer available from Lipoid Corp.

The above formulation had a pH of 7.35 and a viscosity of 3026 rpm (6 rpm 1 min).

The study design was for each of the 11 participants to use one of the two products at least every two hours during a full work day. The participants were instructed that the purpose of the study was to determine preferences between the 2 products for hand disinfection and other product characteristics. The participants were instructed that they would use one product for an entire day and the second product would be used on the next day. They were also instructed to complete a form giving their opinions of the characteristics of the products. The characteristics the participants were asked to evaluate were the feeling when rubbed on, the smell, the after feel, the nature of the experience and whether the product moisturized or dried the hands. The results are provided in tabular form in the following table where, as stated above, "O" represents the sanitizer of this invention and "V" was Purell®.

| Feeling when rubbed on | | | | |
| --- | --- | --- | --- | --- |
|   | Smooth | Silky | Tacky | Greasy |
| O | 7 | 2 | 0 | 2 |
| V | 4.5 | 0.5 | 5 | 1 |

| Smell | | | |
| --- | --- | --- | --- |
|   | Like | Do not like | No Smell |
| O | 5.5 | 1 | 4.5 |
| V | 1.5 | 8 | 1.5 |

| After feel | | | | |
| --- | --- | --- | --- | --- |
|   | Smooth | Silky | Tacky | Greasy |
| O | 9 | 1 | 1 | 0 |
| V | 5 | 1 | 4 | 1 |

| Experience | | | |
| --- | --- | --- | --- |
|   | Pleasing | Adequate | Not pleasing |
| O | 7 | 4 | 0 |
| V | 1.5 | 4.5 | 5 |

| Does this sanitizer moisturize your hands | | |
| --- | --- | --- |
|   | YES | NO |
| O | 9 | 2 |
| V | 4 | 7 |

| Does this sanitizer dry your hands | | |
| --- | --- | --- |
|   | YES | NO |
| O | 3 | 8 |
| V | 7 | 4 |

The "O" sanitizer was found to be statistically superior to Purell® "V" in all categories (p=0.01 or greater).

Example 2: Comparison of Sanitizer to Purell Commercial Product with Physicians

Example 1 was repeated substituting 7 physicians in their own office settings for the 11 members of the general public. All 7 physicians used an alcohol hand sanitizer in their practice, with use varying from 6 times to over 40 times per day. All 7 reported a drying effect when using the Purell hand sanitizer. The study design was for each of the 7 physicians to use one of the two products during their work day in lieu of any other hand sanitizer. The physicians were informed that the purpose of the study was to determine if there was any difference in the performance between the 2 products for hand disinfection. The instructions and the methodologies employed in Example 2 were otherwise the same as employed in Example 1. The results are presented in tabular form.

| Feeling when rubbed on | | | | |
| --- | --- | --- | --- | --- |
|   | Smooth | Silky | Tacky | Greasy |
| O | 4 | 3 | 0 | 0 |
| V | 3 | 0 | 4 | 0 |

| Smell | | | |
| --- | --- | --- | --- |
|   | Like | Do not like | No Smell |
| O | 5 | 0 | 2 |
| V | 2 | 4 | 1 |

| After feel | | | | |
| --- | --- | --- | --- | --- |
|   | Smooth | Silky | Tacky | Greasy |
| O | 5 | 2 | 0 | 0 |
| V | 3 | 0 | 4 |   |

| Experience | | | |
| --- | --- | --- | --- |
|   | Pleasing | Adequate | Not pleasing |
| O | 6 | 1 | 0 |
| V | 2 | 1 | 4 |

| Does this sanitizer moisturize your hands | | |
| --- | --- | --- |
|   | YES | NO |
| O | 5 | 2 |
| V | 0 | 7 |

-continued

| Does this sanitizer dry your hands | | |
| --- | --- | --- |
| | YES | NO |
| O | 2 | 5 |
| V | 7 | 0 |

The results for the moisturizing and drying performance were statistically superior for the sanitizer "O" compared to "V" Purell® (p=0.02) despite the relatively small sample.

Example 3: Comparison of Sanitizer to CVS Instant Hand Sanitizer with Aloe

A comparison of two hand sanitizers was conducted, one using a commercially available CVS ethyl alcohol [65%] hand sanitizer containing aloe and vitamin E to help dryness by acting as a moisturizer "CV", and the other the Example 1 "O" sanitizer of this invention. The comparison was conducted with 5 physicians. The 5 physicians habitually used an alcohol hand sanitizer in their practice with use varying from 8 times to over 30 times per day. All 5 reported a drying effect using the alcohol hand sanitizer. The purpose of this study was to compare the characteristics of the commercially marketed CVS instant hand sanitizer with aloe and Vitamin E to the Example 1 hand sanitizer.

The study design was for each of the 5 physicians to use one of the two products during their work day in lieu of any other hand sanitizer. The physicians were informed that the purpose of the study was to determine if there was any difference in the performance between the 2 products for hand disinfection. The instructions and the methodologies employed in Example 3 were otherwise the same as used in Example 1. The results are presented in tabular form as follows:

| Feeling when rubbed on | | | | |
| --- | --- | --- | --- | --- |
| | Smooth | Silky | Tacky | Greasy |
| O | 4 | 1 | 0 | 0 |
| CV | 1 | 1 | 3 | 0 |

| Smell | | | |
| --- | --- | --- | --- |
| | Like | Do not like | No Smell |
| O | 4 | 0 | 1 |
| CV | 3 | 1 | 1 |

| After feel | | | | |
| --- | --- | --- | --- | --- |
| | Smooth | Silky | Tacky | Greasy |
| O | 3 | 2 | 0 | 0 |
| CV | 1 | 2 | 3 | 0 |

| Experience | | | |
| --- | --- | --- | --- |
| | Pleasing | Adequate | Not pleasing |
| O | 4 | 1 | 0 |
| CV | 1 | 1 | 3 |

| Does this sanitizer moisturize your hands | | |
| --- | --- | --- |
| | YES | NO |
| O | 4 | 1 |
| CV | 1 | 4 |

| Does this sanitizer dry your hands | | | |
| --- | --- | --- | --- |
| | YES | NO | NO OPINION |
| O | 0 | 5 | 0 |
| CV | 3 | 1 | 1 |

The results show that the O sanitizer was preferred to the CV sanitizer.

Example 4: Performance vs. Concentration of Phospholipid

Four formulations were prepared corresponding to the formulation of Example 1 except that the concentration of Phospholipon 75 was differed in each formulation. The procedure of Example 1 was also used for purposes of evaluation using four members of the general public. The concentration of Phospholipon 75 in each of the four formulations is given in the following table:

| Formulation No. | Phospholipon Concentration |
| --- | --- |
| 1 | 0.5 |
| 2 | 1.0 |
| 3 | 1.5 |
| 4 | 2.0 |
| 5 | 2.5 |

Formulation 1 did not adequately provide the benefits of this invention. Formulation 2 was marginal. The remaining formulations 3 through 5 all provide good results and were essentially the same.

The examples illustrate the advantage of adding an anionic phospholipid to a sanitizer containing an antimicrobial concentration of an alcohol. It should be noted that use of a phospholipid that does not contain an anionic component in a high concentration alcohol sanitizer having the composition disclosed herein is also efficacious with respect to improving the feel of the sanitizer on the skin following multiple applications by reducing the tacky feel and drying of the skin following multiple use. However, there is a greater improvement when the anionic phospholipid comprises a portion of the total phospholipid content as described herein.

| Alcohol | 55 to 95 | 60 to 75 |
| --- | --- | --- |
| Phospholipid | 1.0 to 3.0 | 1.5 to 3.5 |
| Emollient | 1.0 to 8.0 | 3.0 to 6.0 |
| Rheology Modifier | 2.5 to 8.0 | 3.5 to 6.5 |
| Emulsifier | 0.1 to 3.5 | 0.5 to 2.5 |
| Water | to 100 | to 100 |

As will be explained in greater detail below, the sanitizer may be formulated using a phospholipid that contains an anionic phospholipid as one component. For this reason, the preferred compositions given above define a range for the phospholipid which may be all anionic phospholipid, or a portion of the total phospholipid additive provided that the anionic portion is present in an amount of from 0.10 weight percent to 3.0 percent of the sanitizer, and more preferably, from 0.25 weight percent to 2.5 percent.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for sanitizing skin, the method comprising:
applying a sanitizer to the skin in the form of a gel or a cream, the sanitizer having a pH of at least 6.8 and comprising:
at least 60 weight percent of a C1 to C4 alcohol;
a rheology modifier and optionally at least one emollient and/or at least one emulsifier, the rheology modifier being selected from the group consisting of carboxylic acid polymers, crosslinked polyacrylate polymers, polyacrylamide polymers, polysaccharides, and combinations thereof; and
an anionic phospholipid in an amount of at least 0.1 weight percent of the sanitizer.

2. The method of claim 1, wherein the anionic phospholipid is present in an amount of from 0.25 to 2.5 percent of the sanitizer.

3. The method of claim 1, wherein the anionic phospholipid is added as a component of a phospholipid mixture and is present in the phospholipid mixture in an amount of at least 5 weight percent of the total phospholipid content.

4. The method of claim 3, wherein the anionic phospholipid component is present in the phospholipid mixture in an amount of between 8 and 15 weight percent and the phospholipid mixture is free of cationic phospholipids.

5. The method of claim 3, wherein the anionic phospholipid is phosphatidylethanolamine.

6. The method of claim 1, wherein the emollient is present in the amount of from 1.0 to 8.0 weight percent of the sanitizer.

7. The method of claim 1, wherein the emulsifier is present in the amount of from 0.1 to 3.5 weight percent of the sanitizer.

8. The method of claim 1, wherein the rheology modifier is present in the amount of from 2.5 to 8.0 percent of the sanitizer.

9. The method of claim 1, wherein the rheology modifier is an acrylates copolymer.

10. A method of forming a sanitizer composition, the method comprising:
forming a sanitizer in the form of a gel or a cream, the forming the sanitizer comprising:
adding an anionic phospholipid to an alcohol to form a first mixture;
heating the first mixture to a temperature of 30° C. to form a first homogeneous solution;
cooling the first homogeneous solution to room temperature;
adding a water soluble moisturizer to water to form a second homogeneous solution;
after the cooling, combining the first homogeneous solution, the second homogeneous solution, and a rheology modifier to form a second mixture, the rheology modifier being selected from the group consisting of carboxylic acid polymers, crosslinked polyacrylate polymers, polyacrylamide polymers, polysaccharides, and combinations thereof; and
agitating the second mixture to form the sanitizer, the sanitizer having a pH of at least 6.8, the alcohol being present in an amount of at least 55 percent by weight of the sanitizer, and the anionic phospholipid being present in an amount of at least 0.10 percent by weight of the sanitizer.

11. The method of claim 10, wherein the anionic phospholipid is present in an amount from 0.25 to 2.5 percent by weight of the sanitizer.

12. The method of claim 10, wherein the anionic phospholipid is added as a component of a phospholipid mixture and is present in the phospholipid mixture in an amount of at least 5 percent by weight of the phospholipid mixture.

13. The method of claim 12, wherein the phospholipid mixture is free of cationic phospholipids.

14. The method of claim 10, wherein the anionic phospholipid is phosphatidylethanolamine.

15. The method of claim 10, wherein the alcohol is present in an amount of at least 60 percent by weight of the sanitizer.

16. The method of claim 10, wherein the alcohol is a C1 to C4 alcohol and is present in an amount from 60 to 75 percent by weight of the sanitizer.

17. The method of claim 10, wherein the pH is from 7.0 to 8.0.

18. The method of claim 10, wherein the rheology modifier is present in an amount to provide a viscosity of at least 2,500 cps.

19. The method of claim 10, wherein the rheology modifier is present in an amount of at least 2.5 percent by weight of the sanitizer.

20. The method of claim 10, wherein the rheology modifier is a crosslinked polyacrylate polymer present in an amount of from 2.5 to 8.0 weight percent of the sanitizer.

21. The method of claim 10 further comprising an emollient selected from the group consisting of oils, aloe, fatty esters, glycerol esters, propylene glycol esters, alkoxylated carboxylic acids, alkoxylated alcohols, fatty alcohols, fatty acids, and combinations thereof present in an amount of from 1.0 to 8.0 percent by weight of the sanitizer.

22. The method of claim 10 further comprising an emollient selected from the group consisting of isopropyl-palmitate, isopropyl-myristate, aloe, and mixtures thereof and is present in an amount from 3.0 to 6.0 percent by weight of the sanitizer.

23. The method of claim 10, wherein the rheology modifier is an acrylates copolymer.

24. A method of forming a sanitizing composition, the method comprising:
forming a sanitizing composition, the forming the sanitizing composition comprising:
mixing a phospholipid mixture, an emollient, an emulsifier, and one or more alcohols having from 1 to 4 carbon atoms to form a first mixture;
heating the first mixture to 30° C. to form a first homogeneous mixture;
the phospholipid mixture comprising an anionic phospholipid;
the emollient being selected from the group consisting of oils, aloe, fatty esters, glycerol esters, propylene glycol esters, alkoxylated carboxylic acids, alkoxylated alcohols, fatty alcohols, fatty acids, and combinations thereof;
the emulsifier being selected from the group consisting of esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, triethanolamine (TEA) stearate, diethanolamine (DEA) oleth-3 phosphate, polyethylene glycol 20 sorbitan monolaurate (polysorbate 20), sorbitan monostearate (Span 60), polyethylene glycol (PEG) 5 soya sterol, steareth-2, steareth-20, steareth-21, ceteareth-20, polypropylene glycol 2 (PPG-2) methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and combinations thereof;

cooling the first homogeneous mixture to room temperature;

mixing a water soluble moisturizer with water to form a second homogeneous mixture;

adding the second homogeneous mixture and a rheology modifier to the first homogeneous mixture to form the sanitizing composition;

the rheology modifier being selected from the group consisting of carboxylic acid polymers, cross-linked polyacrylate polymers, polyacrylamide polymers, polysaccharides, and combinations thereof;

the one or more alcohols being present in an amount of at least 55 percent by weight of the sanitizing composition;

the phospholipid mixture being present in an amount of at least 1 percent by weight of the sanitizing composition;

the emollient being present in an amount from 1 percent to 8 percent by weight of the sanitizing composition;

the rheology modifier being present in an amount from 2.5 percent to 8.0 percent by weight of the sanitizing composition; and the emulsifier being present in an amount from 0.1 percent to 3.5 percent by weight of the sanitizing composition.

25. The method of claim 24, wherein the anionic phospholipid is selected from the group consisting of phosphoglycerides, phosphatidylethanolamine, and combinations thereof.

26. The method of claim 24, wherein the rheology modifier is an acrylates copolymer.

\* \* \* \* \*